United States Patent [19]

Chamberlin et al.

[11] Patent Number: 4,820,671

[45] Date of Patent: Apr. 11, 1989

[54] REGENERATION OF AN ORGANOURANIUM CATALYST

[75] Inventors: Thomas A. Chamberlin; James C. Stevens, both of Midland, Mich.

[73] Assignee: The Dow Chemical Company, Midland, Mich.

[21] Appl. No.: 142,167

[22] Filed: Jan. 11, 1988

[51] Int. Cl.$^4$ .................. B01J 31/40; B01J 38/10; C07F 5/00; C07C 2/26

[52] U.S. Cl. .................. 502/53; 502/30; 502/31; 502/152; 502/158; 534/11; 585/511

[58] Field of Search .......... 502/53, 152, 30, 31; 585/511; 534/11

[56] References Cited

U.S. PATENT DOCUMENTS

| | | | |
|---|---|---|---|
| 3,260,770 | 7/1966 | Hambling | 260/683.15 |
| 3,488,367 | 1/1970 | Fischer et al. | 534/11 |
| 3,676,523 | 7/1972 | Mason | 260/683.15 |
| 3,816,372 | 6/1974 | Lugli et al. | 534/11 |
| 4,341,531 | 7/1982 | Duranleull | 48/197 R |
| 4,642,337 | 2/1987 | Arhaudet et al. | 534/11 |
| 4,695,669 | 9/1987 | Stevens et al. | 585/511 |
| 4,772,734 | 9/1988 | Dubois et al. | 502/152 |

OTHER PUBLICATIONS

Chemical Abstracts 92:146350k.
Chemical Abstracts 106:87444b.
Chemical Abstracts 68:63103k.
R. G. Bowman et al., J. Chem. Soc., Chem. Commun., (1981), 257–258.
J. M. Mandriquez et al., J. Am Chem. Soc. 100, 3939–3940 (1978).
P. B. Hitchcock et al., J. Chem. Soc., Chem. Commun., (1983), 561–563.

Primary Examiner—Paul E. Konopka
Attorney, Agent, or Firm—Marie F. Zuckerman

[57] ABSTRACT

A proces for regenerating a spent catalyst comprising uranium and a poly-substituted cyclopentadienyl ligand comprising contacting the deactivated catalyst with hydrogen under reaction conditions. The regenerated catalyst is active in the selective dimerization of propylene to 4-methyl-1-pentene.

21 Claims, No Drawings

REGENERATION OF AN ORGANOURANIUM CATALYST

BACKGROUND OF THE INVENTION

This invention relates to a process for regenerating an organouranium catalyst.

It is known that organouranium complexes are homogeneous catalysts for the selective dimerization of propylene to 4-methyl-1-pentene. Specifically, U.S. Pat. No. 4,695,669 discloses homogeneous catalysts comprising uranium di(poly-substituted cyclopentadienyl) hydride complexes for such a dimerization. Typically, the selectivity of these catalysts to 4-methyl-1-pentene is at least 94 percent with respect to all $C_6$ products, as well as with respect to other $C_6$ olefins; and often the selectivity is much higher. These uranium catalysts do not exhibit long lifetimes: hence, commercial application of the catalysts is costly and impractical.

In general, the industrial use of homogeneous catalysts is hampered by difficulties in recovering and recycling these catalysts. A homogenous catalyst is a soluble complex comprising inorganic and/or organic ligands and one or more metals. Generally, the deactivation of the homogeneous catalyst occurs because the complex has decomposed and can no longer participate in the catalytic cycle. For example, the ligands, which form a crucial part of the homogeneous catalyst, might slowly react and dissociate from the metallic center. With loss of ligands the metal might precipitate from the reaction solution. It is also possible for several metal centers to react to form a catalytically inactive cluster. Alternatively, a by-product might bind irreversibly to the metal site and terminate the catalytic cycle. The regeneration process must replace the ligands and the metal(s) in a precise structure identical to that of the original active catalyst or catalyst precursor. The reorganization of a decomposed organometallic complex is rarely accomplished in simply one step. Typically, the metal is recovered and the complex is resynthesized. Such is the case, for example, in the regeneration of a spent homogeneous catalyst containing nickel and benzcate ligand, which is used in the oligomerization of ethylene to linear alpha-olefins. (See U.S. Pat. No. 3,676,523).

It would be desirable to have an economical, one-step process of regenerating the catalysts comprising di(poly-substituted cyclopentadienyl)uranium hydride complexes, cited hereinbefore. Such a regeneration process would render these uranium catalysts viable for commercial use in dimerizing propylene to 4-methyl-1-pentene.

SUMMARY OF THE INVENTION

The invention is a process for regenerating a spent catalyst which is susceptible to regeneration, the spent catalyst containing uranium and a poly-substituted cyclopentadienyl ligand. The process comprises contacting the deactivated uranium catalyst with hydrogen under conditions sufficient to regenerate the activity of the catalyst in the dimerization of propylene to 4-methyl-1-pentene.

The regeneration process of this invention is a simple, one-step procedure. The unexpected regeneration of spent catalysts containing uranium and a poly-substituted cyclopentadienyl ligand by the simple process of this invention increases the commercial value of these catalysts for use in catalytic reactions, particularly the dimerization of propylene to 4-methyl-1-pentene.

4-Methyl-1-pentene is useful as a monomer or as a co-monomer in the production of polyolefins.

DETAILED DESCRIPTION OF THE INVENTION

The catalysts which can be regenerated by the process of this invention include any catalyst containing uranium and a poly-substituted cyclopentadienyl ligand. The catalysts may be active in any catalytic reaction; but, preferably, the catalysts are active in the dimerization of propylene to 4-methyl-1-pentene. It is to be understood that repeated use of the catalysts in any catalytic cycle leads to deactivation. The exact nature of the deactivated or spent catalysts is not completely known: therefore, preferred catalysts or catalyst precursors are described hereinbelow as they appear before deactivation occurs.

In addition to the catalyst containing uranium and a poly-substituted cyclopentadienyl ligand, as mentioned hereinabove, the catalyst should be susceptible to the regeneration process of this invention. It has been found that the catalyst can become spent by two pathways. One of these pathways leads to a spent catalytic species which is susceptible to regeneration by the process of this invention. The other pathway leads to a spent catalytic species which is not susceptible to regeneration by this process. It is believed that the spent species which is not susceptible to regeneration arises from the catalyst's extreme sensitivity to oxygen and moisture; although the invention should not be limited in any way by such a theory. Thus, by repeated handling and recycling more of the catalyst is transformed into a species which is irreversibly deactivated. Preferably, the spent catalyst which is susceptible to regeneration has not been recycled more than about 5 times. More preferably, the spent catalyst which is susceptible to regeneration has not been recycled more than about 15 times; most preferably, more than about 25 times.

Preferred catalysts to be employed in the present invention include uranium bis(poly-substituted cyclopentadienyl)-hydride or -allyl complexes. The more preferred catalysts are represented generally by the formula:

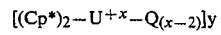

wherein Cp* is a poly-substituted cyclopentadienyl ligand, U is uranium; Q is H or an allylic moiety; x represents the valence of uranium, and is 3 or 4 when Q is H, or 3 when Q is an allylic moiety; and y is 1 or 2. Preferably, each Cp* independently is a moiety of the formula:

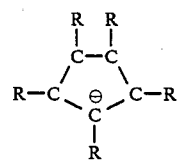

wherein each R independently is H, alkyl of up to about 6 carbon atoms, or alkyl-substituted silyl such as trimethylsilyl, triethylsilyl, and the like with the proviso that at least about two R moieties are not H. Preferably, at least five R moieties are not hydrogen; more preferably, each R is methyl.

The more preferred uranium hydride catalysts are represented generally by the formula:

$$[(Cp^*)_2-U^{+x}-H_{(x-2)}]_y$$

wherein Cp*, U, x and y are as defined previously; and preferably, y is 2. Examples of catalysts which can be employed in the process of the present invention include bis(pentahaptotetramethylcyclopentadienyl)uranium hydride, bis(pentahaptobutyltetramethylcyclopentadienyl)uranium hydride, bis(pentahaptoethyltetramethyloycyclopentadienyl)uranium dihydride, bis(pentahaptopentamethylcyclopentadienyl)uranium hydride, and bis[pentahapto-bis(trimethylsilyl)cyclopentadienyl]uranium hydride. Bis(pentahaptopentamethylcyclopentadienyl)uranium hydride is known to exist as a dimer (y=2) in which uranium is present as an equilibrium mixture of the +3 and +4 valences. Accordingly, the number of hydride ligands can equal 1 and 2 for this compound:

$$[Cp^*_2UH_2]_2 \rightleftharpoons [Cp^*_2UH]_2 + H_2$$

The most preferred uranium hydride catalyst is bis(pentahaptopentamethylcyclopentadienyl)uranium hydride, which also has been reported to catalyze the hydrogenation of olefins. (R. G. Bowman et al., Journal of the Chemical Society, Chemical Communications, 257–258 (1981)).

The active uranium hydride catalysts can be prepared as described hereinbelow, or alternatively, can be generated in situ by subjecting a solution of a catalyst precursor in the form of a uranium bis(poly-substituted cyclopentadienyl) complex to gaseous or dissolved hydrogen in order to pre-form the hydride catalyst. Preferred catalyst precursors for this in situ catalyst generation can be represented by the formula:

$$(Cp^*_2)UR'_2$$

wherein each R' independently can be a hydrocarbon moiety or a silicon-containing hydrocarbon moiety; and U and Cp* are as described previously. Most preferably, Cp* is pentahaptopentamethylcyclopentadienyl.

The term "hydrocarbon" is well-known to those skilled in organic chemistry and refers to a moiety or compound consisting essentially of atoms of carbon and hydrogen. Hydrocarbon moieties can be aromatic or aliphatic, can be saturated or unsaturated, can have carbon chains which are branched, cyclic or straight, and can have mixtures of these attributes. Preferred hydrocarbon moieties have up to about 20 carbon atoms and include alkyl, alkenyl, aryl, alkaryl or aralkyl. Examples of hydrocarbon moieties include methyl, ethyl, butyl, allyl, phenyl, benzyl and the like. Lower alkyl and lower alkenyl of up to about 7 carbon atoms are more preferred. Most preferred is methyl. It is noted that allylic uranium complexes can act as catalysts (Q=allyl) or as catalyst precursors (R'=allyl).

The term "silicon-containing hydrocarbon" refers to hydrocarbons, as defined hereinabove, which contain at least one atom of silicon. Examples of silicon-containing hydrocarbon moieties include trimethylsilylmethyl, bis(trimethylsilyl)methyl, ethyldimethylsilylmethyl, diethylmethylsilylmethyl, and the like. Preferably, the silicon-containing hydrocarbon contains up to about 7 carbon atoms. More preferably, the silicon-containing hydrocarbon is trimethylsilylmethylmethyl.

The preparations of bis(pentamethylcyclopentadienyl)uranium alkyls and hydride are reported in J.A.C.S. by Juan M. Mandriquez et al., Vol. 100, pp. 3939–3941 (1978). The preparations of di[bis(trimethylsilyl)cyclopentadienyl]uranium dichloride and di[bis(trimethylsilyl)cyclopentadienyl]uranium dialkyls, including trimethylsilylmethyls, are reported by Peter B. Hitchcock et al. in J. Chem. Soc. "Chem. Commun.," pp. 561–563 (1983).

In the more preferred uranium catalysts where Q in the general formula is allyl, x is preferably 3 and y is preferably 1. The allylic moiety can be a π-bonded or σ-bonded ligand. Catalysts having π-bonded allylic moieties are represented by the formula:

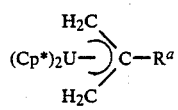

wherein the double bond is delocalized; whereas, catalysts having σ-bonded allylic moieties are represented by the formula:

$$(Cp^*)_2U-CH_2-\underset{R^a}{C}=CH_2$$

wherein $R^a$ is H, a hydrocarbon moiety or a silicon-containing hydrocarbon moiety. Preferably, $R^a$ is H, an alkyl of up to about 6 carbon atoms, or a silicon-containing hydrocarbon of up to about 7 carbon atoms. Most preferably, $R^a$ is H or methyl. Examples of uranium allylic catalysts of the present invention include bis(pentahaptopentamethylcyclopentadienyl)allyluranium, bis[pentahapto-bis(trimethylsilyl)cyclopentadienyl]allyluranium and bis(pentahaptopentamethylcyclopentadienyl)(2-methylallyl)uranium. The most preferred catalyst is bis(pentahaptopentamethylcyclopentadienyl)allyluranium.

The catalyst complexes wherein Q is allyl can be prepared by contacting an allylic alkylating agent and a bis(poly-substituted cyclopentadienyl)uranium (IV) dihalide in an inert solvent under reaction conditions sufficient to form a bis(poly-substituted cyclopentadienyl)(bromo or chloro)(allyl)uranium (IV) complex. The preparation of bis(poly-substituted cyclopentadienyl)uranium (IV) dihalide complexes is well-known. For example, the preparation of bis(pentamethylcyclopentadienyl)uranium (IV) dichloride is reported by Juan M. Manriquez et al. in J.A.C.S. op.cit. The preparation of di[bis(trimethylsilyl)cyclopentadienyl]uranium (IV) dichloride is reported by Peter B. Hitchcock et al. in J. Chem. Soc., "Chem. Comm.," op.cit. Preferred bis(poly-substituted cyclopentadienyl)uranium (IV) dihalides are represented by the formula U(Cp*)$_2$X$_2$ wherein Cp* is as defined hereinabove, and X is preferably independently Cl or Br, most preferably Cl.

Allylic alkylating agents are well-known in the art and include compounds of the formula:

$$Q_n\text{-M-}X_m$$

wherein Q is an allylic moiety as previously defined, M is a metallic element, and X is an anionic ligand. Preferred anionic ligands include fluoride, chloride, bromide or iodide. The value of n can range from 1 to 4, and m can range from 0 to a value high enough to satisfy the valence requirements of the metallic element. The allylic alkylating agent can exist as a monomeric species, or as a dimer, trimer, or higher oligomer, and optionally can contain additionally coordinated metal salts. Preferred metallic elements include Li, Na, K, Rb, Cs, Be, Mg, Ca, Ti, Zr, Al, Cu, Ag, Zn, Cd, Hg, Sn, and Pb. Silicon, although not generally considered to be a metallic element, can also be employed. More preferred metallic elements are Li, Na, Mg and K. The most preferred alkylating agents are allyl lithium, allyl magnesium chloride, allyl magnesium bromide, 2-methylallyl magnesium chloride, and 2-methylallyl magnesium bromide.

The preferred reaction stoichiometry is one mole of bis(poly-substituted cyclopentadienyl)uranium dihalide to one mole of allylic alkylating agent. Higher mole ratios of allylic alkylating agent to bis- (poly-substituted cyclopentadienyl)uranium dihalide can result in over-alkylation and the formation of undesirable bis(poly-substituted cyclopentadienyl)uranium bis(allyls) or even tris(allyl)(poly-substituted cyclopentadienyl)uranium. Over-alkylation is less likely when the allylic moiety has more steric bulk than unsubstituted allyl ($C_3H_5$). For example, an excess of 2-substituted allylic alkylating agent can be successfully employed.

The reaction of the bis(poly-substituted cyclopentadienyl)uranium dihalide with the allylic alkylating agent preferably is conducted in a solvent. Any solvent can be used for the reaction with the proviso that the solvent is substantially inert with respect to degradation of the uranium species as well as the allylic alkylating agent. Ethers are preferred solvents for the reaction of the allylic alkylating agent with the bis(poly-substituted cyclopentadienyl)uranium dihalide. Diethyl ether is the most preferred solvent.

The reaction temperature for the preparation of the bis(poly-substituted cyclopentadienyl)(chloro or bromo)(allyl)uranium (IV) complex is not critical. It is preferred that the temperature is below the decomposition temperature of the allylic alkylating agent as well as the decomposition temperature of the uranium species, and that the temperature is high enough for the reaction to proceed at a convenient rate. For the sake of convenience, room temperature is the preferred temperature of the reaction of the allylic alkylating agent with the bis(poly-substituted cyclopentadienyl)uranium dihalide. The reaction preferably is carried out in an environment which is substantially free of oxygen and water.

When the bis(poly-substituted cyclopentadienyl)uranium dihalide and an allylic alkylating agent are contacted under reaction conditions as described hereinabove, a bis(poly-substituted cyclopentadienyl)(bromo or chloro)(allyl)uranium (IV) complex is produced. Preferred complexes are represented by the formula (Cp*)$_2$UQX wherein Cp*, U, Q and X are defined hereinbefore.

The active allylic complexes of the present invention can be prepared by contacting the bis(poly-substituted cyclopentadienyl)(monohalo)(monoallyl)uranium (IV) complex with a reducing agent in an inert solvent under reaction conditions sufficient to form the bis(poly-substituted cyclopentadienyl)(allyl)uranium (III) complex. The reducing agent serves to convert the inactive uranium (IV) complex to the active U(III) catalyst of the present invention. Preferred reducing agents are elemental metals, or amalgams of metals with mercury. Most preferred is sodium amalgam. A stoichiometric amount or an excess of the reducing agent can be successfully employed for the reduction process. Preferably, the reducing agent is not able to coordinate to the bis(poly-substituted cyclopentadienyl)(allyl)uranium (III) product, as additional ligands may be detrimental to the catalytic propylene dimerization reaction. For example, the use of elemental hydrogen (H2) as a reducing agent is detrimental, as hydrogen leads to the formation of trimeric uranium (III) bis(poly-substituted cyclopentadienyl) chloride. See Fagan et al., *Organometallics*, Vol. 1, pp 170–80 (1982).

The reaction temperature for the reduction process is not critical. However, it is preferred that the temperature is below the decomposition temperatures of the reducing agent and the uranium species, and that the temperature is high enough for the reaction to proceed at a convenient rate. Room temperature is the preferred temperature of the reduction process for the sake of convenience.

When a bis(poly-substituted cyclopentadienyl)-(monohalo)(monoallyl)uranium (IV) complex and a reducing agent are contacted under reaction conditions as described hereinabove, the bis(poly-substituted cyclopentadienyl)uranium (III) allylic complex is produced. Preferred catalyst complexes are represented by the formula (Cp*)$_2$UQ, wherein Cp*, U and Q are as defined hereinabove.

The catalysts of this invention, whether active or spent, are sensitive to oxygen, water, and other materials which provide a source of acidic protons. Accordingly, it is preferred that the catalyst, whether active or spent, be stored in a substantially inert environment, so as to avoid irreversible degradation. Such inert environments include inert gases such as nitrogen, helium, neon, argon, krypton, xenon, and saturated lower alkanes, such as methane or ethane.

Any of the catalysts and catalyst precursors identified hereinbefore can be contacted with propylene in a manner described in U.S. Pat. No. 4,695,669, incorporated herein by reference. Under reaction conditions the dimerization of propylene occurs to yield 4-methyl-1-pentene in high selectivity. Eventually, the catalyst loses activity. The process of this invention as described hereinbelow will serve to regenerate substantially the original activity and selectivity of the catalyst.

The spent catalyst may be used in the regeneration process of this invention as a solid; or optionally, the spent catalyst may be dissolved in a suitable solvent. Any aliphatic or aromatic hydrocarbon which does not react with the spent or regenerated catalyst, with hydrogen, and with any optional carrier gases is a suitable solvent. Mixtures of said aliphatic and aromatic hydrocarbons may also be suitably employed. Preferably, the solvent is a saturated aliphatic hydrocarbon, such as pentane, heptane, or dimethylbutane, or a monocyclic aromatic hydrocarbon, such as benzene, toluene, or xylene. More preferably, the solvent is toluene. The amount of solvent employed will depend on the particular catalyst and the particular circumstances. Typically, enough solvent is employed to dissolve all of the spent catalyst. Preferably, the amount of solvent will vary from about 90 weight percent to about 99.9 weight percent of the total solution.

Hydrogen in the form of gaseous elemental hydrogen is used in the process of this invention to regenerate the aforementioned catalysts. Depending on the design of the reactor, the hydrogen may be used as an undiluted gas, or alternatively, may be dissolved in solution. Optionally, an inert carrier gas may be mixed with the hydrogen gas, if desired. By "inert" it is meant that the carrier gas does not react with the spent or regenerated uranium catalyst, with hydrogen, and with any solvent which is present. Examples of suitable inert carrier gases include nitrogen, argon, helium, neon, krypton, and lower aliphatic hydrocarbons, such as methane, ethane, pentane and n-butane. The amount of hydrogen employed will depend on the amount of spent catalyst to be regenerated. Typically, the mole ratio of hydrogen relative to the original active organouranium catalyst or catalyst precursor is at least about 1.0. Preferably, the mole ratio of hydrogen to original active organouranium catalyst or catalyst precursor is at least about 2.0.

The deactivated organouranium catalyst and hydrogen are contacted in any manner which yields the reactivated catalyst. For example, the solid catalyst may be placed in a fixed-bed and the hydrogen passed through the bed. Alternatively, the catalyst may be dissolved in a solvent and the hydrogen introduced above the solution. Preferably, the catalyst is dissolved in a solvent and hydrogen is introduced above the solution.

The hydrogen pressure employed in the process of this invention is any operable pressure which produces the regenerated catalyst. Typically, the pressure is a function of several variables, including the amount of deactivated catalyst, the volume of the reactor, and the temperature; and therefore ranges from subatmospheric to superatmospheric. Generally, the pressure is in the range from about 0.5 psia to about 500 psia. Preferably, the pressure is in the range from about 100 psia to about 200 psia. More preferably, the pressure is in the range from about 15 psia to about 100 psia. Below the preferred lower limit there may be insufficient hydrogen concentration in the vicinity of the deactivated catalyst to regenerate the catalyst to any useful extent. Above the preferred upper limit the process may be difficult or costly to operate.

The temperature at which the deactivated organouranium catalyst is contacted with hydrogen is any temperature which assures the regeneration of the deactivated catalyst. Typically, the temperature can vary from about −100° C. to about 200° C. Preferably, the temperature is in the range from about 0° C. to about 100° C. More preferably, the temperature is about ambient, taken as about 20° C. Below the preferred lower temperature limit the regeneration of the catalyst may be too slow. Above the preferred upper temperature limit the catalyst may begin to decompose.

The spent catalyst is exposed to hydrogen for a time sufficient to regenerate at least partially the spent catalyst. The time can vary depending on the process conditions, most particularly the hydrogen pressure. Typically, however, the exposure of the spent catalyst to hydrogen is for a time in the range from about 5 minutes to about 5 hours. Preferably, the exposure is for a time in the range from about 10 minutes to about 3 hours. More preferably, the exposure is from about 30 minutes to about 2 hours. Below the preferred lower time limit the spent catalyst is not regenerated to any useful extent. Above the preferred upper time limit the catalyst is sufficiently regenerated, and there is no additional benefit from continued exposure to hydrogen.

The degree of regeneration of the spent catalyst depends on the length of exposure to hydrogen, on the reaction conditions, specifically temperature and pressure, and on the number of regenerations of the same sample. Preferably, at least 30 percent of the catalytic activity is regenerated by the process of this invention. More preferably, at least 60 percent of the catalytic activity is regenerated by the process of this invention. Most preferably, at least 80 percent of the catalytic activity is regenerated by the process of this invention. The degree of regeneration can decrease with each successive regeneration of the same sample. Typically, the regeneration process begins to lose efficiency at about the fourth or greater regeneration cycle.

The process of this invention extends the lifetime of the organouranium catalysts in the dimerization of propylene to 4-methyl-1-pentene. Advantageously, the high selectivity to 4-methyl-1-pentene is maintained by the regenerated catalyst. Generally, a catalyst of this invention has an average lifetime from about 165 hours to about 200 hours at which time about 98 percent of the catalyst is dead. Depending on the number and length of the regeneration cycles, the lifetime of the catalyst can be increased to from about 450 hours to about 750 hours. Thus, the productivity of the catalyst is significantly increased by the practice of this invention. Preferably, the productivity of the catalyst is increased by about 170 percent. More preferably, the productivity of the catalyst is increased by about 200 percent. Most preferably, the productivity of the catalyst is increased by about 275 percent.

The invention is illustrated by the following experiments, which should not be construed to be limiting of the scope thereof. Cp* represents the pentamethylcyclopentadienyl moiety in the Examples.

EXAMPLE 1

Part A—Preparation of Spent Catalyst

All solvents and internal standards are distilled from Na/K under argon. Hydrogen (Scott Specialty Gases, 99.9995 percent ultrapure grade) is employed.

$(Cp^*)_2U(CH_2SiMe_3)_2$, wherein Cp* is defined hereinabove and Me is methyl, is prepared by the procedure of P. J. Fagan et al., J. Am. Chem. Soc., 103, 6652 (1981).

A 500-ml glass flask fitted with a valved sampling port is thoroughly oven dried at 110° C. for 16 hours. After drying, the flask is transferred to the antechamber of an inert atmosphere glove box. The flask is opened and loaded with $Cp^*U(CH_2SiMe_3)_2$ (105.7 mg, 0.158 mmole), 20.0 ml of toluene, 25 μof 2,2-dimethylbutane and 25 μl of heptane to form a solution. (The dimethylbutane and heptane are used as internal standards in the analysis of the reaction.) The flask is sealed, removed from the glove box, and attached to a vacuum line where the solution is degassed by two 10-minute freeze-pump-thaw cycles at a temperature of −196° C. and a pressure of 10−2 mm Hg. After the second thaw cycle, the catalyst is activated by filling the flask with hydrogen at a pressure of 1 atmosphere, and vigorously stirring the solution for thirty minutes. After the activation the flask is again subjected to a freeze-pump-thaw cycle to remove excess hydrogen; thereafter, the system is pressurized to 1 atmosphere with propylene and stirred vigorously. The flask is tightly sealed and transported into the glove box, where the solution is stirred and sampled over a period of 166 hours.

Aliquots of the propylene dimerization reaction are analyzed on a Hewlett-Packard 5880 capillary gas chromatograph fitted with a 60 meter J & W Narrow Bore Capillary Column (0.25μ) bonded with DB-1. The propylene dimerization reaction is found to proceed according to the equation:

$$[dimer] = (k_r/k_d)[cat]_o[propylene]_o(1-\exp(-k_d t))$$

wherein [dimer] is the concentration of the dimeric product at time t, $k_r$ is the rate constant of the olefin dimerization reaction, $k_d$ is the rate constant of the deactivation reaction, $[cat]_o$ is the initial concentration of catalyst, $[propylene]_o$ is the initial concentration of propylene, and t is the time. Solution of the equation by regression analysis leads to values for the two rate constants, as shown in Table I. The ratio of the final concentration of active catalyst to the initial concentration of active catalyst, $[cat]_f/[cat]_o$, is calculated to be 0.021, as shown in Table I. Thus, nearly 98 percent of the catalyst is inactivated in 166 hours. The flask is again tightly sealed and transferred to the vacuum line, whereupon all of the volatile materials are removed at ambient temperature and a pressure of $10^{-2}$ mm Hg. The solid, non-volatile resi- due in the flask constitutes the spent catalyst.

Part B

(1) Regeneration of Spent Catalyst

The spent catalyst of Part A hereinabove, which is contained in an evacuated 500 ml glass flask, is transferred to the glove box of Part A. To the flask is added toluene, 2,2-dimethylbutane and heptane as in Part A to make a solution. The flask is sealed, removed from the glove box, and attached to the vacuum line where the solution is degassed by two 10-minute freeze-pump-thaw cycles at a temperature of $-196°$ C. and a pressure of $10^{-2}$ mm Hg. After the second thaw cycle, the catalyst is regenerated by filling the flask with hydrogen at a pressure of 1 atmosphere and vigorously stirring the solution for 1 hour. After the regeneration is complete, the flask is subjected to a second freeze-pump-thaw cycle to remove excess hydrogen. The regenerated catalyst remains in the toluene solution; but may be isolated by pumping under vacuum at ambient temperature and a pressure of $10^{-2}$ mm Hg to remove the solvent and the chromatography standards.

(2) Propylene Dimerization Using Regenerated Catalyst

The regenerated catalyst is tested in the dimerization of propylene in a manner identical to the procedure of Part A. The glass flask containing the regenerated catalyst, toluene and the chromatography standards, is pressurized to 1 atmosphere with propylene and stirred vigorously. The flask is tightly sealed and transported into the glove box, where the solution is stirred and sampled over a period of 167 hours. Aliquots of the reaction are analyzed by gas chromatography as previously described. The rate constants are calculated from the rate equation of Part A, and are given in Table I. Since the spent catalyst of Part A is 98 percent inactive, the observed rate constant, $k_r$, for the regenerated catalyst is a measure of the amount of regeneration attained. The percentage regeneration is therefore given by the general formula:

$$k_r(\text{regenerated})/k_r(\text{initial}) \times 100$$

and in this first regeneration is:

$$(3.55 \times 10^{-4})/(4.42 \times 10^{-4}) \times 100 = 80.3\%$$

(See Table I.) The flask is again tightly sealed and transferred to the vacuum line, whereupon all of the volatile materials are removed at ambient temperature and a pressure of $10^{-2}$ mm Hg leaving another residue of spent catalyst.

EXAMPLES 2–4

The procedures of Example 1, Part B (1 & 2), are repeated three more times with the spent catalyst from Example 1, Part B. In each regeneration cycle the hydrogenation time is varied with the results tabulated in Table I.

TABLE I

| Ex. | $H_2$ Time (hrs) | $k_r$ [1] | $k_d$ [2] | $[cat]_f/[cat]_o$ [3] | % Regeneration [4] |
|---|---|---|---|---|---|
| 1A | ... | 4.42 | 0.65 | 0.021 | ... |
| 1B | 1.0 | 3.55 | 0.50 | 0.049 | 80.3 |
| 2 | 1.5 | 2.20 | 0.35 | 0.125 | 62.0 |
| 3 | 2.0 | 1.36 | 0.35 | 0.124 | 61.8 |
| 4 | 2.5 | 0.14 | 0.48 | 0.058 | 10.3 |

[1] Rate constant of dimerization reaction × $10^4$ l/mole · sec
[2] Rate constant of deactivation reaction × $10^5$ sec$^{-1}$
[3] Fraction of active catalyst at end of dimerization.
[4] Based on $k_r$(regenerated)/$k_r$(initial)

It is seen that more than 60 percent of the spent catalyst is regenerated on each of the second (Example 2) and third (Example 3) successive regenerations using the process of the invention. The productivity of the catalyst is increased by over 200 percent.

What is claimed is:

1. A process for regenerating a spent catalyst containing a uranium (poly-substituted cyclopentadienyl) complex, said catalyst being susceptible to regeneration, wherein the process comprises contacting the deactivated uranium catalyst with hydrogen under conditions sufficient to regenerate the activity of the catalyst in the dimerization of propylene to 4-methyl-1-pentene.

2. The process of claim 1 wherein the catalyst is a bis(poly-substituted cyclopentadienyl)uranium -hydride or -allyl complex.

3. The process of claim 2 wherein the bis(poly-substituted cyclopentadienyl)uranium -hydride or -allyl complex is represented by the formula:

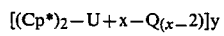

$$[(Cp^*)_2-U+x-Q_{(x-2)}]y$$

wherein Cp* is a poly-substituted cyclopentadienyl ligand; U is uranium; Q is H or an allylic moiety; x is the valence of uranium, and is 3 or 4 when Q is H, and x is 3 when Q is an allylic moiety; and y is 1 or 2.

4. The process of claim 4 wherein Cp* is a moiety of the formula;

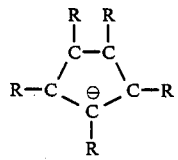

wherein each R is independently selected from the group consisting of H, alkyl of up to about 6 carbon atoms and alkyl substituted silyl with the proviso that at least about two R moieties are not H.

5. The process of claim 4 wherein each R is methyl.
6. The process of claim 3 wherein Q is H.
7. The process of claim 6 wherein the uranium catalyst is bis(pentahaptopentamethylcyclopentadienyl)uranium hydride.
8. The process of claim 3 wherein Q is an allylic moiety.
9. The process of claim 8 wherein the catalyst contains a π-bonded allylic moiety and is represented by the formula;

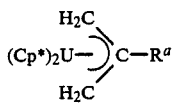

wherein $R^a$ is H, an alkyl moiety of up to 6 carbon atoms, or a silicon-containing hydrocarbon of up to 7 carbon atoms.

10. The process of claim 8 wherein the catalyst contains a σ-bonded allylic moiety and is represented by the formula;

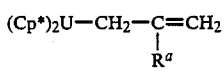

wherein $R_a$ is H, an alkyl moiety of up to 6 carbon atoms, or a silicon-containing hydrocarbon of up to 7 carbon atoms.

11. The process of claim 8 wherein the complex is bis-(pentahaptopentamethylcyclopentadienyl)allyluranium.

12. The process of claim 1 wherein the catalyst has originally been prepared in situ from a catalyst precursor, which is represented by the formula;

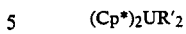

wherein Cp* is a poly-substituted cyclopentadienyl moiety, and each R' is independently a hydrocarbon moiety or a silicon-containing hydrocarbon moiety of up to about 7 carbon atoms.

13. The process of claim 12 wherein the catalyst precursor is bis(pentahaptopentamethylcyclopentadienyl)-bis(trimethylsilylmethyl)uranium.
14. The process of claim 1 wherein the temperature is in the range from about −100° C. to about 200° C.
15. The process of claim 1 wherein the pressure is in the range from about 0.5 psia to about 500 psia.
16. The process of claim 1 wherein the contact time is in the range from about 5 minutes to about 5 hours.
17. The process of claim 1 wherein the mole ratio of hydrogen to original active catalyst is at least about 1.
18. The process of claim 1 wherein at least 30 percent of the catalytic activity is regenerated compared with the activity of the initial catalyst.
19. The process of claim 1 wherein at least 60 percent of the catalytic activity is regenerated compared with the activity of the initial catalyst.
20. The process of claim 1 wherein at least 80 percent of the catalytic activity is regenerated compared with the activity of the initial catalyst.
21. The process of claim 1 wherein the productivity of the catalyst is increased by about 200 percent compared with the productivity of the fresh catalyst.

* * * * *